United States Patent [19]

Margolis et al.

[11] Patent Number: 4,619,270
[45] Date of Patent: Oct. 28, 1986

[54] INFANT RESPIRATORY ARREST STIMULATOR DEVICE

[76] Inventors: Frederick J. Margolis, 2134 Waite Ave.; Clayton K. Cole, 1821 Hillsdale, both of Kalamazoo, Mich. 49008

[21] Appl. No.: 600,498

[22] Filed: Apr. 16, 1984

[51] Int. Cl.⁴ ............................................... A61B 5/05
[52] U.S. Cl. ..................................... 128/721; 128/782
[58] Field of Search ................................. 128/721–723, 128/716, 774, 782; 340/573, 575

[56] References Cited

U.S. PATENT DOCUMENTS

| | | | |
|---|---|---|---|
| 3,325,799 | 6/1967 | Farris | 128/721 X |
| 3,658,052 | 4/1972 | Alter | 128/721 |
| 3,796,208 | 3/1974 | Bloice | 128/721 X |
| 3,950,799 | 4/1976 | Frank | 128/721 X |
| 4,066,072 | 1/1978 | Cummins | 128/716 X |

FOREIGN PATENT DOCUMENTS 2081454 2/1982 United Kingdom ................ 128/782

Primary Examiner—William E. Kamm
Assistant Examiner—Angela D. Sykes
Attorney, Agent, or Firm—Flynn, Thiel, Boutell & Tanis

[57] ABSTRACT

An infant respiratory arrest stimulator device which includes a frame and a crib pivotally supported on the frame about a generally horizontally extending axis. The crib has a generally horizontally aligned child supporting surface and sidewalls extending upwardly therefrom adjacent the perimeter of the supporting surface. A drive motor is mounted on the frame and has an output member rotatable about a generally horizontal axis of rotation. A crank arm is secured to the rotatable output member and a connecting structure is provided for drivingly connecting the crank arm to the crib at a location spaced perpendicularly away from the axis of rotation of the crib to thereby effect a pivoting motion of the crib about its axis of rotation in response to a rotation of the output member. A control is provided for controlling the frequency and amplitude of the pivoting motion. Additional structure is provided for initiating a rotation of the output member in response to an occurrence of an apnea and bradycardia episode to a child located on the supporting surface of the crib, so that the child will be vigorously shaken by the rapid movement of the supporting surface the moment an apnea and bradycardia episode is detected.

9 Claims, 9 Drawing Figures

INFANT RESPIRATORY ARREST STIMULATOR DEVICE

FIELD OF THE INVENTION

The present invention relates to an apnea monitoring and therapeutic system and, more specifically, a system directed at stimulation of an infant in respiratory arrest.

BACKGROUND OF THE INVENTION

Sudden infant death is unpredictable and exhaustive studies have been made to determine ideology which is yet to be accurately defined. The cessation of respiration often referred to as apnea and the diminution of heart rate often referred to as bradycardia, are critical problems for all infants and premature infants are especially predisposed. In fact, between the ages of one month and one year, sudden infant death syndrome (SIDS) is the number one cause of death. It is understood that repeated attacks as well as prolonged attacks of apnea are factors which carry a poor prognosis both for life and for subsequent mental development resulting from irreversible cerebral damage sustained during these apneic episodes. Currently, the best prospect for preventing apnea is through constant surveillance, preferably using some automated device to alert attendants so that manual stimulation or resuscitation can begin promptly. As a consequence, apnea monitoring of infants has become a standard practice in both the home and health care institutions.

Management of apnea monitoring in infants for the most part includes sensitive devices for detecting apnea events. Upon detection of an apnea episode, a visual or audible alarm is generated, to call the parent or attending nurse for prompt manual stimulation of the infant in an attempt to terminate the episode by restoring normal breathing and heart rate. Alertness and responsiveness of the parent or nursing staff is important as it becomes more difficult to obtain a positive response to stimulation the longer the apnea and bradycardia persists. Naturally then, most monitors are designed to provide an early alarm. Unfortunately, however, most of these apnea and bradycardia episodes are of a short duration and occur almost randomly during any day of infant life. Thus, they place a continuous burden on the parent or nurse to the extent that in some cases the alarms have been inadvertently neglected.

In most instances, the parents of an infant first discover that their child is subject to apnea and bradycardia episodes only after the child is in the home. If the child survives this episode, it will be one of very few that do. Current statistics reveal that only a few children per year survive an apnea episode whereas approximately 10,000 per year do not survive. It has become current practice to place the monitoring system within the home of the child. Thus, the alertness and responsiveness of the parents becomes vitally important. After many weeks of this alertness and responsiveness, the parents virtually become exhausted and there have been many instances where the parents have slept through the alarm resulting in the death of the infant.

While we are not unmindful of the subject matter of U.S. Pat. No. 3,950,799 which discloses a respiratory distress stimulator system, it has been our experience to note that children susceptible to apnea and bradycardia episodes will return to normal breathing and cardiac activity if vigorously manually stimulated as by shaking and/or jostling. However, if the parent, or in some instances, nursing personnel are not immediately at hand, this vigorous stimulation shaking of the child cannot be performed. As has been noted in the aforementioned U.S. Pat. No. 3,950,799, it becomes more difficult to obtain a positive response to stimulation the longer the apnea and bradycardia persists. Thus, the earlier that a child is vigorously stimulated, the more likely it is that the child will survive.

Accordingly, it is an object of this invention to provide an infant respiratory arrest stimulator device that will effect a vigorous shaking of the child immediately in response to the detection of an apnea and/or bradycardia episode by a monitoring device.

It is a further object of this invention to provide an infant respiratory arrest stimulator device, as aforesaid, wherein the conventional apnea monitoring devices do not need to be structurally altered, thus making it possible for the respiratory arrest stimulator device to be immediately put to use with conventional respiratory/cardiac monitoring equipment.

It is a further object of this invention to provide an infant respiratory arrest stimulator device, as aforesaid, wherein the crib in which the child has been placed is vigorously shaken in instantaneous response to the detection of an apnea and bradycardia event.

It is a further object of this invention to provide an infant respiratory arrest stimulator device, as aforesaid, wherein in addition to a vigorous shaking of the child located in a crib, loud and sharp noise pulses are generated by structure on the crib in an effort to startle the child back to a normal breathing cycle.

It is a further object of this invention to provide an infant respiratory arrest stimulator device which is reliable and durable and requires little or no maintenance.

It is a further object of this invention to provide an infant respiratory arrest stimulator device, as aforesaid, wherein the device can be tested periodically to make sure that it works properly and includes an indicating mechanism indicating to the attendant whether there has been an activation of the respiratory arrest stimulator device in the absence of any direct interaction with the child by the attendant.

SUMMARY OF THE INVENTION

The objects and purposes of the invention are met by providing an infant respiratory arrest stimulator device which includes a frame and a child supporting surface movably supported on the frame. The child supporting surface has sidewalls extending upwardly therefrom adjacent the perimeter of the supporting surface. A drive motor is mounted on the frame and has a movable output member. A connecting structure is provided for drivingly connecting the output member to the movable child supporting surface to thereby effect a moving of the child supporting surface in response to a rotation of the output member. A control is provided for controlling the frequency and amplitude of the movement. Additional structure is provided for initiating a rotation of the output member in response to an occurrence of an apnea and bradycardia episode to a child located on the supporting surface of the crib, so that the child will be vigorously shaken by the rapid movement of the supporting surface the moment an apnea and bradycardia episode is detected.

BRIEF DESCRIPTION OF THE DRAWINGS

Other objects and purposes of this invention will be apparent to persons acquainted with apparatus of this general type upon reading the following specification and inspecting the accompanying drawings, in which.

DETAILED DESCRIPTION

Figure 1:
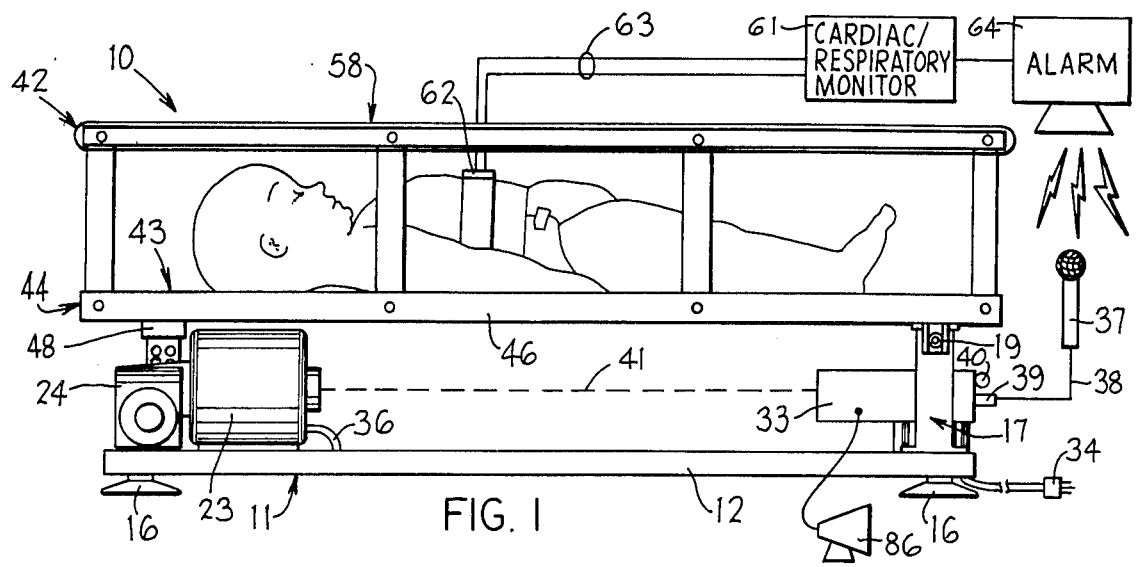
FIG. 1 is a side elevational view of the infant respiratory arrest stimulator device embodying the invention, the bedding materials having been omitted for purposes of clearer illustration of a child located therewithin.
Figure 2:
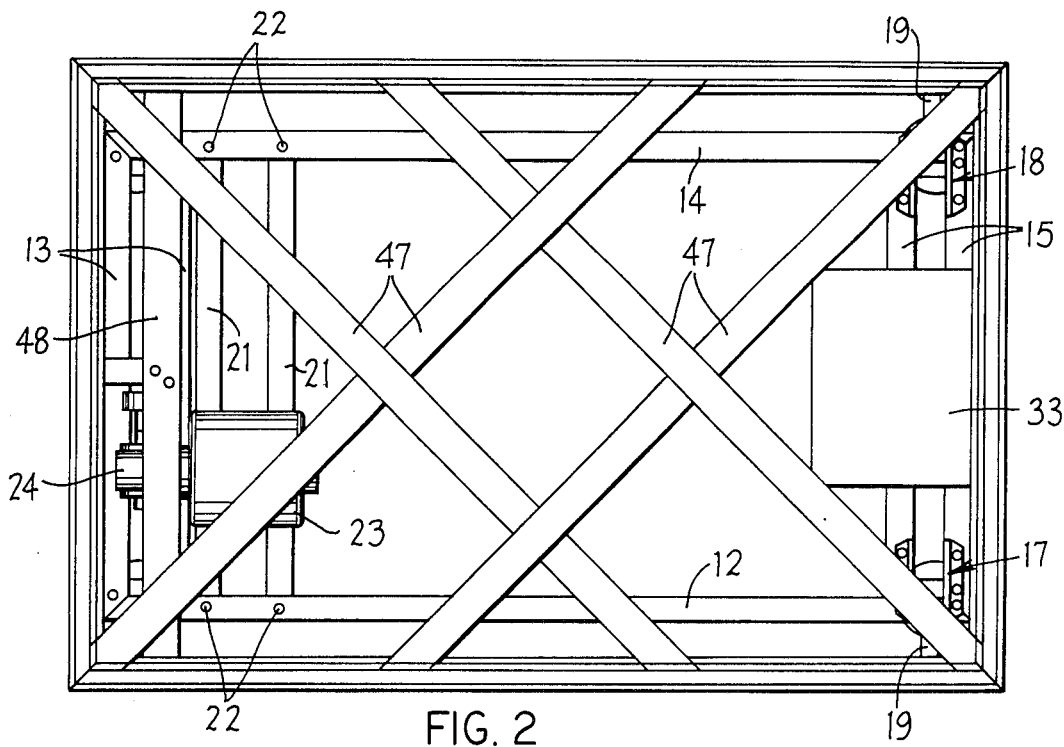
FIG. 2 is a top elevational view of the respiratory arrest stimulator device.
Figure 3:
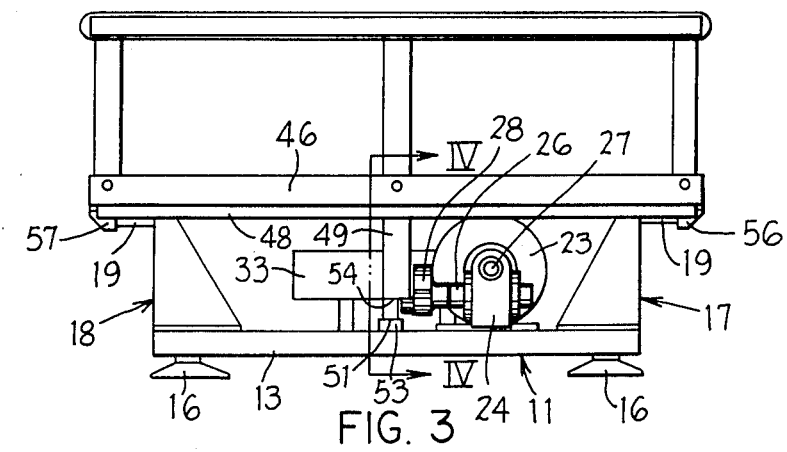
FIG. 3 is a left end view of the respiratory arrest stimulator device.

A first embodiment of the infant respiratory arrest device 10 illustrated in FIGS. 1 to 4 includes a substantially rectangular frame 11 having side piece members 12, 13, 14 and 15 secured at their ends by fasteners. In this embodiment, the side piece members 13 and 15 each include a pair of side-by-side side piece members extending parallel to each other. A suction cup 16 is secured to the underside of the frame adjacent each of the four corners thereof.

A pair of stanchions 17 and 18 are mounted on the upper side of the frame 11 and on one of the side-by-side side piece members. In the embodiment illustrated in FIGS. 1 to 4, the stanchion members 17 and 18 are both mounted on the two side piece members 15. Each stanchion member 17 and 18 has a pivot bearing 19 mounted thereon. In this particular embodiment, the pivot axes for the pivot bearing are coaxial and extend parallel to the side piece member 15.

The frame 11 also includes a pair of parallel support bars 21 extending parallel to the side piece members 13 and 15 and having their ends fixedly secured to the side piece members 12 and 14, as by fasteners 22. In this particular embodiment, the support bars 21 are located closely adjacent the side piece member 13, namely, at the opposite end of the frame from the stanchion members 17 and 18. An electric motor 23 is mounted on and secured to the support bars 21. A gear reducing mechanism 24 is mounted on the side piece members 13 and its input is coupled directly to the output shaft of the motor 23. In this particular embodiment, the output shaft 26 of the gear reducing mechanism 24 is oriented at a right angle to the output shaft 27 (FIG. 3) for the motor 23. A crank arm member 28 is secured to the output shaft 26 of the gear reducing mechanism 24 and is rotatable therewith. A roller 29 is rotatably secured to the crank arm member on a side thereof facing away from the gear reducing mechanism 24. In this particular embodiment, the axis of rotation 31 of the roller 29 is radially offset from the axis of rotation 32 (FIG. 4) of the output shaft 26 and the crank arm member 28.

A conventional control module 33 is mounted on the frame and, in this particular embodiment, is secured to the side piece members 15 intermediate the stanchions 17 and 18. Electrical energy is supplied to the control module 33 through the electrical cord 34 which can be plugged into any conventionally available 120-volt power source, such as the electrical supply source available in any residence. Electrical energy is supplied from the control module 33 through an electrical cord 36 to the motor 23. The control module 33 has a microphone jack receptacle thereon. A microphone 37 is connected through an appropriate cable 38 to a jack 39 receivable in the microphone jack receptacle on the control module 33. The circuitry within the control module 33 is adapted to convert sound picked up by the microphone 37 into a signal which energizes the motor 23 through the electric cord 36 and thereby effecting a rotation of the crank arm 28. The ability of the control module 33 to control the energization of the electric motor 23 is schematically indicated by the broken line 41 in FIG. 1. Further, the control module has an indicator light 40 thereon which becomes energized during operation of the motor and stays illuminated until turned off by an attendant.

Figure 4:
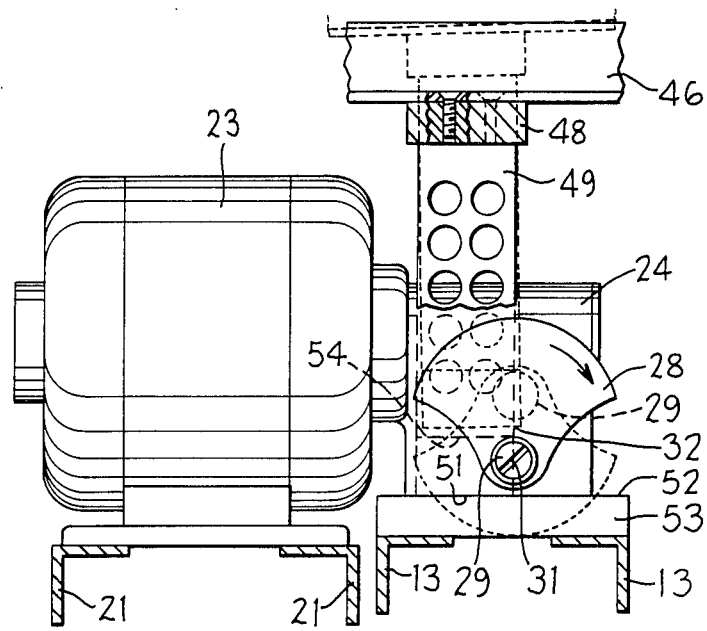
FIG. 4 is a sectional view taken along the line IV—IV of FIG. 3.

A crib 42 includes a generally horizontally aligned child supporting surface defined by a rectangular frame 44. The frame is composed of plural side pieces 46 connected to form a rectangle and the child supporting surface 43 is defined by cross bracing members 47 connected to and extending between the side piece members 46. In this particular embodiment, a further crosspiece 48 is connected to and extends on the underside of the frame 44 in a direction parallel to and is oriented immediately above the side piece members 13. A bar member 49 is secured to and extends downwardly from the crosspiece 48 intermediate the ends thereof. In this particular embodiment, the lower end 51 of the bar 49 is flat and normally rests on the upper surface 52 of an anvil member 53 secured to the side piece members 13 (FIG. 4). Further, the bar 49 is stepped as at 54 with the downwardly facing surface of the step being in radial alignment with the roller 29 on the crank arm 28. Thus, as the crank arm is rotated, the roller will move into engagement with the downwardly facing surface of the step 54 to effect a lifting of the bar 49 and the frame 44 connected thereto.

The end of the frame 44 remote from the crosspiece 48 has a pair of coaxially aligned hinge pins 56 and 57 secured thereto, which hinge pins are received in the pivot bearings 19 mounted on the stanchions 17 and 18. Thus, a lifting of the bar 49, as aforesaid, will effect a pivotal movement of the frame about the axis of the coaxially aligned hinge pins 56 and 57 received in the axially aligned pivot bearings 19.

For the protection of the child located on the child supporting surface 43, an upstanding side frame construction 58 is provided. Normally, bedding would be provided on the child supporting surface 43 and on the inside of the side frame construction 58 to provide comfort to the child while lying in the crib 42.

The apnea and bradycardia monitor 61 could take the configuration of a number of conventional monitors now commercially available irrespective of whether the basis of their operation is based on the impedance pneumography, capacitance respirometry, or any other technique for detecting the apnea and bradycardia episode. A typical one of such monitors is shown in FIG. 1. Further types of monitors are depicted in U.S. Pat. No.

3,950,799. A sensor 62 is secured by suitable means to a child, and the respiratory and cardiac activity is detected by this sensor 62 and is converted to an electrical signal which is conducted by the leads 63 to the monitor 61. Respiratory and cardiac problems are detected by the monitor 61 to cause signals indicative of apnea and bradycardia episodes to be generated for energizing an alarm 64. The sound emitted by the alarm is picked up by the microphone and, as stated above, effects an energization of the electrical motor 23 to effect a rotation of the crank arm 28.

Referring now in detail to the specific orientation of the roller 29 on the crank arm 28 to the downwardly facing surface of the step 54, it is to be noted that the roller 29 is movable in an orbit about the axis of rotation 32 for the crank arm 28. This orbital movement will cause the roller to engage the downwardly facing surface of the step 54 to effect, upon a continued movement of the roller about the axis of rotation 32, an upward movement of the bar 49. Upon reaching the uppermost limit of the orbit, the roller 29 will be oriented at the broken line position thereof illustrated in FIG. 4. At this particular point, the roller will move out of engagement with the downwardly facing surface of the step 54 so that the bar 49 will be permitted to fall freely downwardly so that the downwardly facing surface 51 of the bar 49 will strike the anvil member 53 and emit a sharp sound.

We have discovered that a vigorous shaking of the child will occur when the frequency of the up-and-down movements of the frame 44 about the pivot axis for the pivot bearings 19 is in the range of 100 to 260 cycles per minute. A lower range of frequency will be ineffective for vigorously shaking the child and higher cycles will cause the frame 11 to become disengaged from the surface upon which it is mounted and literally dance. In this latter instance, the suction cups 16 will be insufficient to hold the frame securely to the supporting surface upon which they are mounted. Further, in order to achieve optimum shaking of the child, we have discovered that the peak-to-peak amplitude for the vertical movement of the bar 49 is to be in the range of ½ inch (1.27 centimeters) to 1½ inches (3.81 centimeters). This frequency and this amplitude of movement will effect a vigorous shaking of the child and will be sufficient to stimulate a child experiencing an apnea and bradycardia episode to a normal breathing cycle and heart rate.

Figure 5:
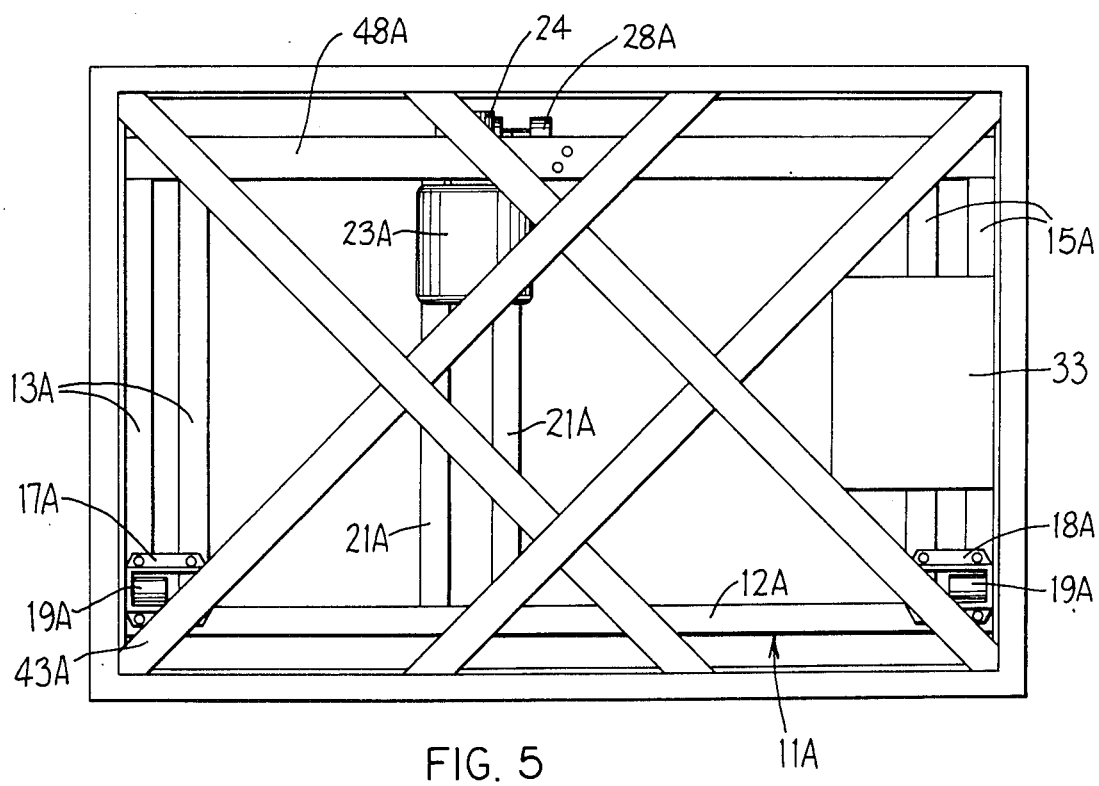
FIG. 5 is a top elevational view of a modified construction for the respiratory arrest stimulator device.

Referring now to FIG. 5, a modified respiratory arrest stimulator device is illustrated therein. For purposes of further discussion, the same reference numerals will be used for this embodiment as were used in the previously discussed embodiment except that the suffix "A" will be added to each reference numeral. The major difference between the embodiment of FIGS. 1 to 4 and the embodiment of FIG. 5 is the location of the pivot bearings 19A and the location of the electrical motor 23 and associated gear reducing mechanism 24. In the embodiment of FIG. 5, the pivot bearings 19A are each located on stanchions 17A and 18A but instead of these stanchions being mounted on the same side piece members as was disclosed in the preceding embodiment, the stanchion members 17 and 18 are each secured to separate side piece members 13A and 15A, respectively. A further difference is that the crosspiece 48A extends parallel to the side piece member 12A of the frame 11A and is located on a side of the frame 11A remote from the pivot bearings 19A. Thus, the bar (not illustrated in this embodiment but corresponding to the bar 49 discussed above) depends downwardly from the crosspiece 48A and operatively engages the roller on the crank arm 28A in the same manner as is illustrated in FIG. 4 and described above. Thus, further comment concerning this particular embodiment is believed unnecessary.

Figure 6:
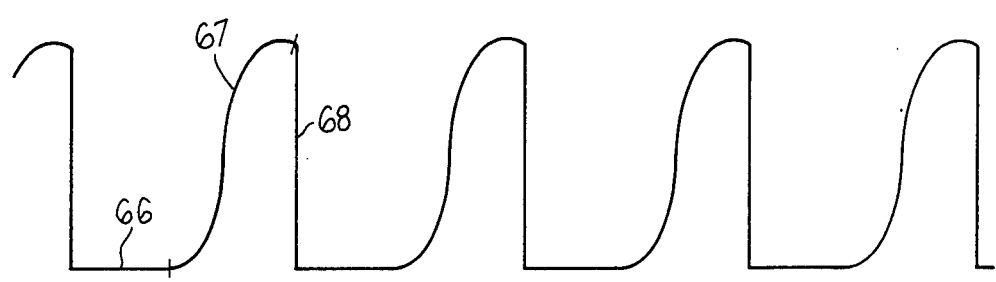
FIG. 6 is a movement waveform generated by the drive mechanism illustrated in FIG. 4.

The waveform of movement generated by the drive motor 23, 23A rotating the crank arm 28 and accompanying roller 29 is illustrated in FIG. 6. While the bottom surface 51 of the bar 49 is engaged with the anvil member 53, no movement of the child supporting surface 43, 43A is generated as depicted by the segment 66 of the waveform illustrated in FIG. 6. As soon as the roller moves into engagement with the downwardly facing surface of the step 54, the surface will be moved upwardly in accordance with the segment 67 of the waveform illustrated in FIG. 6. Upon the roller moving out of engagement with the downwardly facing surface of the step 54, the bar 49 will fall freely downwardly until the downwardly facing surface strikes the anvil member 53 as indicated by the segment 68 of the waveform in FIG. 6. Thereafter, the movement cycle repeats itself.

An important facet of the previously described movement is the sharp downward slope of the segment 68 representing the free fall of the bar 49 until the lower surface 51 thereof engages again the anvil member 53. This sharp fall will startle the infant and when the anvil is struck by the downwardly facing surface 51 on the bar 51, the noise will additionally startle the child. A continued and rapid up-and-down movement accompanied by the rather sharp striking noises of the bar 49 on the anvil member 53 accompanied by the sound of the alarm 64 will be sufficient to startle the youngster back into a normal breathing cycle and heart rate. A reinstitution of the normal breathing cycle will be detected by the control monitor 33 and will shut the alarm off as well as halting the shaking movement of the crib 42.

Figure 7:
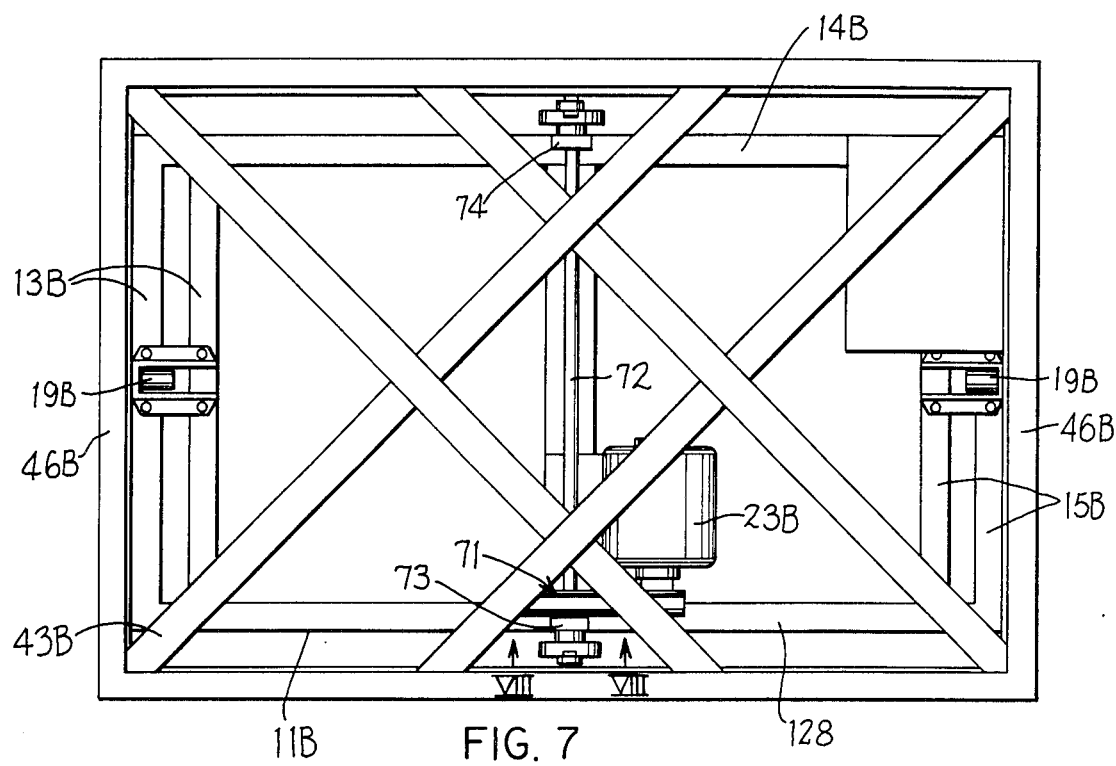
FIG. 7 is a top elevational view of a further modified respiratory arrest stimulator device.
Figure 8:
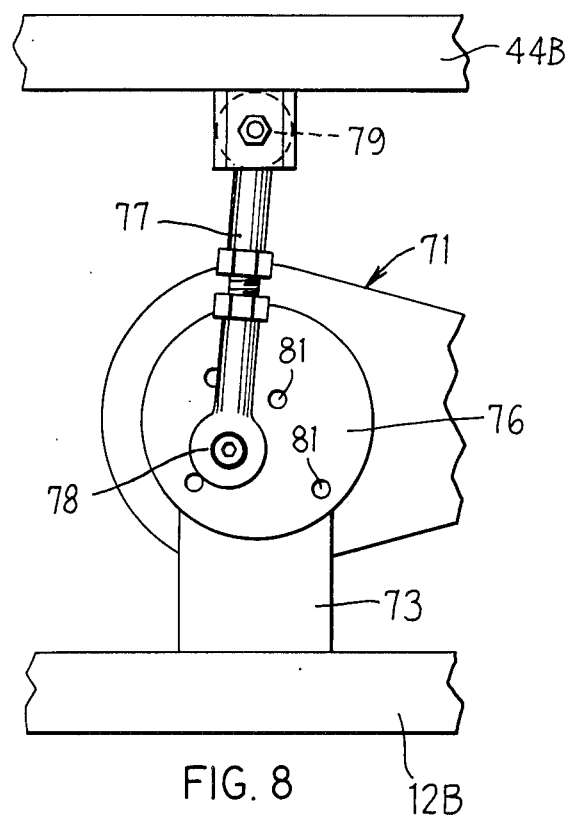
FIG. 8 is a sectional view taken along the line VIII—VIII of FIG. 7.

A further alternate embodiment of the respiratory distress stimulator device is illustrated in FIGS. 7 and 8. In this particular embodiment, the reference numerals that have been used hereinabove will again be used to describe the structure but will have the suffix "B" added thereto. In this particular embodiment, the pivot bearings 19B are supported in a similar manner on the side piece members 13B and 15B but are located at the midlength thereof. Similarly, the child supporting surface 43B is pivotally secured to the pivot bearings 19B midlength along the side piece members 46B thereof which extend parallel to the side piece members 13B and 15B.

The drive arrangement for this particular embodiment is different than the drive arrangement described above. In this embodiment, the electric motor 23B is coupled through a variable speed pulley arrangement 71 to effect a rotation of an elongated shaft 72 which extends generally perpendicular to the pivot axis defined by the axially aligned pivot bearings 19B. The elongated shaft 72 is rotatably supported on stanchions 73 and 74 secured to the side piece members 12B and 14B, respectively, of the frame 11B. In this particular embodiment, a disk 76 is secured to opposite ends of the shaft 72 and both are rotatable therewith. A connecting rod is journalled as at 78 to the disk 76 and as at 79 to the underside of the crib frame 44B as best illustrated in FIG. 8. The vertical movement or stroke of the frame 44B can be controlled by the specific location whereat the connecting rod 77 is journalled to the disk 76. For this purpose, plural holes 81 are provided in the disk to enable the connecting rod 77 to be journalled at varying distances from the axis of the shaft 72.

Figure 9:
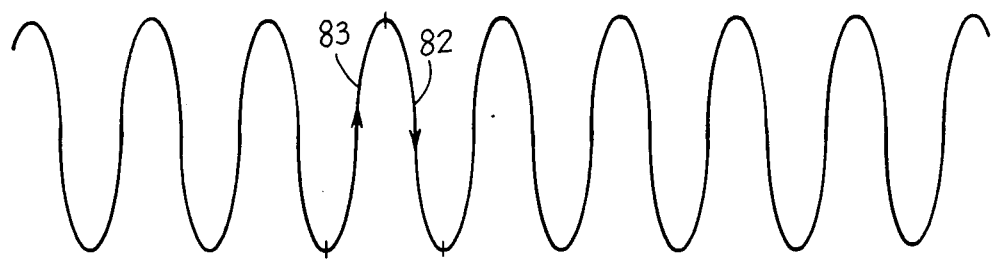
FIG. 9 is a movement waveform generated by the drive mechanism illustrated in FIG. 8.

In this particular embodiment, the frequency and peak-to-peak amplitude of the crib frame 44B adjacent the location whereat the connecting rod 77 is journalled to the frame 44B is approximately the same as for the previously discussed embodiment. The waveform for the movement of the crib frame 44B is illustrated in FIG. 9. The segment of the waveform represented by the reference numeral 82 is nearly vertical as is the upward segment 83. In this embodiment, the child is oriented so that its longitudinal height axis is generally parallel to the pivot axis formed by the pivot bearing 19B. Thus, the child will be vigorously shaken from side to side.

In the event that the infant is so depressed from the apnea and bradycardia episode that it does not respond to the jolting, thumping stimulation and the parent is in a situation that he/she does not hear the alarm signal from the alarm 64, a horn 86 will be activated to initiate a sound of great intensity. It is preferred that activation of the horn occur only after 30 seconds of operation of the motor 23, 23A.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An infant respiratory arrest stimulator device for use with a respiratory/cardiac monitoring system, comprising:
   a frame;
   a crib having a generally horizontal and a movable child supporting surface and sidewalls extending upstandingly therefrom adjacent the perimeter of said movable supporting surface;
   a drive motor mounted on said frame and having a movable output member;
   connecting means for drivingly connecting said output member to said child supporting surface;
   control means for controlling the frequency and amplitude of movement of said child supporting surface, said frequency being in the range of 100 to 260 cycles per minute and said amplitude being in the range of ½ inch to 1½ inches peak to peak; and
   means for initiating a movement of said output member in response to an occurrence of an apnea and bradycardia episode to a child adapted to be located on said supporting surface for effecting a vigorous shaking of the child on said child supporting surface.

2. The infant respiratory arrest stimulator device according to claim 1, wherein said means for initiating a movement of said output member includes a first sound emitting device and a sound pick up device and means responsive to sound picked up by said sound pick up device for activating said drive motor.

3. The infant respiratory arrest stimulator device according to claim 2, including an auxiliary sound emitting device responsive to the emission of sound from said first sound emitting device such that said auxiliary sound emitting device emits a sound of great intensity.

4. An infant respiratory arrest stimulator device for use with a respiratory/cardiac monitoring system, comprising:
   a frame;
   a crib having a generally horizontal child supporting surface and sidewalls extending upstandingly therefrom adjacent the perimeter of said supporting surface;
   pivot means for pivotally supporting said crib on said frame and about a horizontally extending first axis;
   a drive motor mounted on said frame and having an output member rotatable about a generally horizontal second axis of rotation;
   a crank arm secured to said output member;
   connecting means for drivingly connecting said crank arm to said crib at a location spaced perpendicularly away from said first axis of rotation to thereby effect a pivoting motion of said crib about said first axis of rotation in response to a rotation of said output member;
   control means for controlling the frequency and amplitude of said pivoting motion, said frequency being in the range of 100 to 260 cycles per minute and said amplitude being in the range of ½ inch to 1½ inches peak to peak; and
   means for initiating a rotation of said output member in response to an occurrence of an apnea and bradycardia episode to a child adapted to be located on said supporting surface.

5. The infant respiratory arrest stimulator device according to claim 4, wherein said connecting means comprises a roller rotatably secured to said crank arm at a location spaced away from said second axis of rotation so that said roller will orbit about said second axis of rotation in a first vertical plane;
   wherein said frame has an anvil surface thereon;
   wherein a cam member is provided having a generally horizontal cam surface fixed to said crib at a location spaced perpendicularly away from said first axis of rotation and aligned with said vertical plane of orbital movement of said roller and positioned to cause said roller, in response to a rotation of said output member, to engage said cam surface at a point adjacent the location where the orbital movement of said roller changes from a vertically downward movement to a vertically upward movement to thereby effect a lifting of said crib about said first axis of rotation; and
   wherein means is provided on said cam member defining a support surface normally resting on said anvil surface, a generally vertical surface and an abrupt edge between said vertical surface and said horizontal cam surface, said abrupt edge being oriented in a second vertical plane extending parallel to said second axis of rotation whereby said orbital movement of said roller will cause said roller to move past said abrupt edge and enable gravity to abruptly accelerate said crib in a downward direction to cause said child support surface to strike said anvil surface and emit a sound upon contact therewith.

6. The infant respiratory arrest stimulator device according to claim 4, wherein said connecting means comprises a connecting rod journalled at one end thereof to said crank arm and at the other end thereof to said crib.

7. The infant respiratory arrest stimulator device according to claim 6, wherein said control means includes a variable speed drive motor and means for varying the output speed of rotation thereof.

8. The infant respiratory arrest stimulator device according to claim 6, wherein said control means includes means for varying the location on said crank arm at which said connecting rod is journalled.

9. An infant respiratory arrest stimulator device for use with a respiratory/cardiac monitoring system, comprising:

a frame having an anvil surface thereon;

a crib having a generally horizontally aligned baby supporting surface and sidewalls extending upstandingly therefrom adjacent the perimeter of said supporting surface;

pivot means for pivotally supporting said crib on said frame and about a horizontally extending first axis of rotation;

a drive motor mounted on said frame, and having an output member rotatable about a generally horizontal second axis of rotation;

a crank arm secured to said output member;

a roller rotatably secured to said crank arm at a location spaced away from said second axis of rotation so that said roller will orbit about said second axis of rotation in a first vertical plane;

a cam member having a generally horizontal cam surface fixed to said crib at a location spaced perpendicularly away from said first axis of rotation and aligned with said vertical plane of orbital movement of said roller and positioned to cause said roller, in response to a rotation of said output member, to engage said cam surface at a point adjacent the location where the orbital movement of said roller changes from a vertically downward movement to a vertically upward movement to thereby effect a lifting of said crib about said first axis of rotation;

means on said cam member defining a support surface normally resting on said anvil surface, a generally vertical surface and an abrupt edge between said vertical surface and said horizontal cam surface, said abrupt edge being oriented in a second vertical plane extending parallel to said second axis of rotation whereby said orbital movement of said roller will cause said roller to move past said abrupt edge and enable gravity to abruptly accelerate said crib in a downward direction to cause said support surface to strike said anvil surface and emit a sound upon contact therewith; and means for initiating a rotation of said output member in response to an occurrence of an apnea and bradycardia episode to a child adapted to be located on said supporting surface.

* * * * *